United States Patent [19]
Horlenko et al.

[11] 3,962,350
[45] June 8, 1976

[54] CONVERSION OF AROMATIC ALDEHYDES TO PHENOLIC COMPOUNDS

[75] Inventors: Theodore Horlenko; James Henry George, both of Corpus Christi, Tex.

[73] Assignee: Celanese Corporation, New York, N.Y.

[22] Filed: Aug. 26, 1974

[21] Appl. No.: 500,811

Related U.S. Application Data

[62] Division of Ser. No. 33,931, May 1, 1970, Pat. No. 3,850,995.

[52] U.S. Cl. .................................... 260/621 G
[51] Int. Cl.² ................................... C07C 39/06
[58] Field of Search ........ 260/621 R, 621 G, 624 R, 260/599, 600

[56] References Cited
UNITED STATES PATENTS

| | | | |
|---|---|---|---|
| 2,199,585 | 5/1940 | Bone | 260/621 G |
| 2,223,383 | 12/1940 | Moyer | 260/621 G |
| 3,609,195 | 9/1971 | Fields | 260/621 G |
| 3,850,995 | 11/1974 | Horlenko et al. | 260/621 G |
| 3,872,156 | 3/1975 | Bourdin | 260/479 |

OTHER PUBLICATIONS

Buehler, "Chem. Abstract," vol. 70 (1969), p. 96330b.

*Primary Examiner*—James O. Thomas, Jr.
*Assistant Examiner*—W. B. Lone
*Attorney, Agent, or Firm*—Ralph M. Pritchett

[57] ABSTRACT

Phenolic compounds, such as phenol itself, are formed by oxidizing the corresponding aromatic aldehyde precursors, in the vapor phase, with molecular oxygen, the gaseous oxidation product being cooled in the presence of an inert diluent to prevent formation of tarry condensation products. In a particular embodiment a mixture of toluene and benzaldehyde is reacted with oxygen to convert the benzaldehyde to phenol while a portion of the toluene is oxidized to benzaldehyde which is recycled. The products are separated by solvent extraction.

9 Claims, No Drawings

CONVERSION OF AROMATIC ALDEHYDES TO PHENOLIC COMPOUNDS

This is a division, of application Ser. No. 33,931 filed May 1, 1970 now U.S. Pat. 3,850,995.

BACKGROUND OF THE INVENTION

This is a continuation in part of copending patent application Ser. No. 860,027, filed September 22, 1969.

This invention relates to the production of phenolic compounds, e.g. phenol itself. More particularly it relates to the production of a phenolic compound from a corresponding aromatic aldehyde; that is, it relates to a method for replacing the carbonyl group of an aromatic aldehyde with the phenolic hydroxy group.

In a particularly useful embodiment, the invention relates to a method for producing phenol from benzaldehyde, which in turn is obtained by the vapor phase oxidation of toluene to form either benzaldehyde itself or its equivalent precursor benzyl alcohol. The benzyl

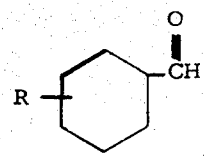

alcohol is oxidized to benzaldehyde, which then is oxidized to phenol.

Taking phenol itself as an example of an industrially useful phenolic compound, the presently-available industrial methods for producing it synthetically comprise (a) sulfonation processes, (b) chlorination processes, (c) the alkylation of benzene to cumene followed by conversion to cumene hydroperoxide which is then split to phenol and acetone, and (d) a two-stage liquid-phase oxidation process in which toluene is catalytically oxidized to benzoic acid which then, in a second stage, is further oxidized to phenol. While these processes are all commercially useful, each has some drawback. For example, the sulfonation and chlorination processes, as well as the liquid-phase oxidation process, entail difficulties due to equipment corrosion, while the cumene hydroperoxide process has, among other drawbacks, the limitation that its economics are dependent in large part on profitable disposal of the by-product acetone. The benzoic acid process is also subject to operating difficulties due to formation of tars in the second reaction step.

Other than the above-identified two-stage oxidation process, processes for producing a phenol by oxidatively converting an alkyl substituent in an aromatic compound are not known.

The art also contains no clear teaching that an aromatic aldehyde, such as benzaldehyde, can be oxidized to form the corresponding phenol in appreciable yield. Barnard and Ibberson, in a paper published in "Combustion and Flame", Vol. 9, pages 149–157 (June, 1965), discuss the gaseous oxidation of toluene and report the presence of trace quantities of phenol in the oxidation products. Yields of phenol were very small, however, and methods for obtaining significant yields of phenol from benzaldehyde are not set forth. These workers also report the formation of tarry deposits in the reaction system.

It is an object of the present invention to provide a method for converting an aromatic aldehyde to the corresponding phenolic compound. It is another object to provide a method for accomplishing said conversion by straightforward oxidation methods which do not require the use of any catalyst. It is another object to provide a method whereby said oxidation can be accomplished with minimum product loss due to tar formation. It is yet another object to provide a method for converting an alkyl benzene to the corresponding phenolic compound by way of an aromatic aldehyde derived from the alkybenzene.

It is particular object to provide an improved process for converting toluene to phenol, in which process the toluene is converted to benzaldehyde which is then further converted to phenol.

Other objects of the invention will be apparent from the following detailed description and examples.

BRIEF SUMMARY OF THE INVENTION

In accordance with the present invention an aromatic aldehyde of the formula:

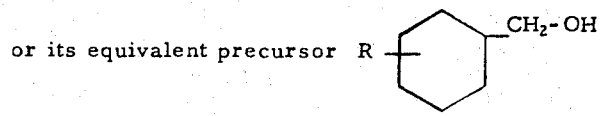

is converted to the corresponding phenolic compound of the formula:

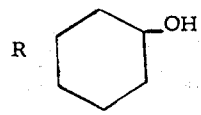

by oxidizing the aldehyde to the phenolic compound with molecular oxygen in the vapor phase to form a gaseous reaction product comprising the phenolic compound, which gaseous reaction product is then cooled in the presence of a diluent liquid whereby the formation of tarry condensation reaction derivatives of the phenolic compound is prevent. In the foregoing formulas, R is a member of the group consisting of hydrogen and alkyl, oxoalkyl, hydroxyalkyl, and hydroxy groups, the term "oxoalkyl" embracing both aldehyde and ketone moieties. The aldehyde can be introduced into the oxidation step either as such or else in the form of the corresponding alcohol, which is the equivalent of the aldehyde in the present process. When the alcohol is employed in place of the aldehyde, it initially oxidizes to the aldehyde, which then undergoes the further oxidation to the corresponding phenol as described above. As will be discussed hereinbelow, certain limitations as to reaction temperature, pressure, and retention time are recommended, as well as preferred methods for bringing the hot gaseous reaction product into contact with the diluent in effecting the cooling step.

A particularly useful embodiment of the invention comprises forming the aromatic aldehyde, such as benzaldehyde, from a hydrocarbon precursor, such as toluene, simultaneously with the oxidation of a portion of the aldehyde to the desired phenolic product, such as phenol itself. In this embodiment, the hydrocarbon precursor (e.g. toluene) is also employed as the diluent, so that there results a novel unitary process for converting the hydrocarbon to the corresponding phenolic compound.

More particularly, the novel process as applied to producing phenol from toluene comprises the following steps:

1. A mixture comprising toluene and benzaldehyde is passed, in the vapor phase, together with molecular oxygen, through a reaction zone which is maintained at an elevated temperature and, preferably, at superatmospheric pressure.
2. In the reaction zone a portion of the toluene is oxidized to form additional quantities of benzaldehyde, this reaction being initiated by the benzaldehyde contained in the mixture fed into the reaction zone initially. Typically, a quantity of benzyl alcohol is also formed from the toluene in this step.
3. A portion of the benzaldehyde is oxidized to phenol in the reaction zone, while a portion remains in the form of benzaldehyde in the gaseous products emerging from the reaction zone. If benzyl alcohol is present in the feed-stock, it is partially oxidized to benzaldehyde.
4. The hot gaseous reaction product continuously withdrawn from the reaction zone, still containing unoxidized toluene, is cooled, preferably rapidly. If the reaction product, under the pressure existing during this cooling step, has a dew point greater than about 200°C, it is recommended that, before it is cooled to its dew point, the dew point be adjusted to a temperature not exceeding about 200°C, by introducing more diluent as discussed above, or by reducing the cooling system pressure, or by admixing steam or an inert fixed gas such as nitrogen or methane into the reaction product being cooled.
5. As the product mixture comprising phenol, benzaldehyde, and toluene is cooled below its dew point, the resulting condensate comprises a mixture of toluene, benzaldehyde, and phenol along with lesser quantities of reaction byproducts. The formation of phenol-benzaldehyde condensation products is inhibited by the presence of the toluene diluent. Without the diluent, a substantial quantity of phenol and benzaldehyde would be lost in condensation reactions, or, even under otherwise very favorable circumstances, there would be excessive fouling of the cooling equipment.
6. The phenol is recovered from the liquefied reaction products, and the benzaldehyde is recycled to the reaction step along with toluene. Phenol precursors such as benzyl alcohol and bibenzyl are also recycled in the preferred embodiment.

It will be recognized that, in the preferred embodiment just described, it is not necessary to pass the diluent toluene (as distinguished from that toluene which is to be oxidized to benzaldehyde) through the reaction zone, although this is convenient. That portion of the toluene which is to serve as diluent in the cooling step of the process can, if desired, be injected in the vapor form into an intermediate stage of the reaction zone, or it can be injected into the gaseous reaction products as they are withdrawn from the reactor. Injection of the diluent toluene as a vapor helps to insure that, when condensation of the reaction products begins, admixture with the diluent will be intimate and of maximum effectiveness. However, it is also within the scope of the invention to quench the reaction products rapidly in liquid toluene without first adding toluene vapor. In this latter event, it is recommended that the reaction product be kept above its dew point before it is brought into contact with the liquid, and that the quenching operation be as rapid as possible and with quick and thorough admixture of the gases into the body of the liquid diluent. Employment of a rapid quench in this manner makes it possible to cool mixtures having dew points of 200°C or higher.

When the preferred embodiment of the process is carried out as described above, with the benzaldehyde being recycled to the reaction step continuously as it is formed, steady-state oxidation reaction conditions develop in which there is a net "make" of phenol from the process with no net make of benzaldehyde. Some benzaldehyde can be drawn off, of course, if desired, with a corresponding decrease in production of phenol.

DETAILED DESCRIPTION OF THE INVENTION

Applicable Chemical Species

As noted above, the invention is broadly applicable to the oxidation of substituted benzaldehydes as well as to benzaldehyde itself. For example, when the R group of the formulae set forth hereinabove is a methyl group, the aromatic aldehyde is a tolualdehyde and the oxidation product is a cresol. Further oxidation of the cresol, as by recycling it to the oxidation step, can be carried out with the result that it is converted to a hydroxy benzaldehyde which is then oxidizable to a dihydroxy benzene such as resorcinol.

When the R group is a higher alkyl group or a substituted alkyl group such as an oxoalkyl or hydroxyalkyl group, exhaustive oxidation of the R group will ultimately convert it to an aldehydo group which then oxidizes to the phenolic hydroxy group. Thus, by repeated recycle of partially oxidized products to the oxidation reaction zone, any ring substituent of the types named above can ultimately be converted to a simple carbonyl group which then oxidizes to the hydroxy group. The most straightforward process obtains, however, in the conversion of benzaldehyde to phenol and, when desired, in the integration of this reaction step with the oxidation of toluene to provide the benzaldehyde or benzaldehyde precursors.

As previously noted, the corresponding aromatic alcohol can be substituted as the equivalent of the aromatic aldehyde the oxidation of which to the corresponding phenol is the subject of this invention. For example, benzyl alcohol is equivalent to benzaldehyde. When the alcohol is employed in the oxidation step in place of the aldehyde, it is oxidized immediately to the aldehyde; i.e., the aldehyde is formed in situ from the alcohol, and is then oxidized to the corresponding phenol. The result is as though the aldehyde itself had been initially introduced into the oxidation reactor.

Oxidation Reaction Conditions

In the oxidation step a catalyst (such as hydrogen bromide which is mentioned in some of the prior art) is not required. The aromatic aldehyde which is to be oxidized, however, does act as an initiator for oxidation of an aromatic hydrocarbon precursor of the aldehyde (such as toluene) in that embodiment of the invention in which the aromatic aldehyde and its hydrocarbon precursor are oxidized together in a cyclic process such as that which has been described for the conversion of toluene to phenol. If desired, other carbonyl compounds such as aldehydes, e.g., acetaldehyde, can be employed to initiate the oxidation of the hydrocarbon precursor to the aromatic aldehyde.

The temperature of the oxidation reaction has been discovered to have a significant effect on product distribution. Specifically, the temperature should be 250°C to 450°C, preferably 275°C to 425°C, and most preferably 325°C to 375°C. The choice of these temperature ranges reflects the discovery that the carboxylic acid corresponding to the aromatic aldehyde being oxidized (e.g., benzoic acid when the aldehyde being oxidized is benzaldehyde), which is not desired to produce, is formed to only a very minor extent between about 325°C and 375°C but that the conversion of the aldehyde to the carboxylic acid begins to increase as the temperature falls below 350°C and also it rises above about 375° to 400°C. Near either end of the broad range identified above, i.e. 250°C to 450°C, significant conversion of the aldehyde to the phenolic compound still takes place, but in a proportion not so satisfactory as that obtaining when the oxidation temperature is above about 300°C and below about 400°C. For example, in oxidizing benzaldehyde to phenol in the presence of toluene at 300°C about 60% of the benzaldehyde was converted to phenol and about 27% to benzoic acid, whereas at 350°C less than 1% was converted to benzoic acid. Practically no benzoic acid formation was observed between 350°C and about 375°C, but at 400°C the formation of benzoic acid again became apparent. At an even higher temperature, i.e. 450°C which is at the upper end of the recommended range, significant conversion of the aldehyde to bicyclic derivatives begins to take place. Specifically, in the case of benzaldehyde oxidation in the presence of toluene bibenzyl formation begins to occur to a substantial extent at 450°C. Bibenzyl can be converted to phenol by recycle to the reaction zone, but it is preferred that as much benzaldehyde as possible be converted directly to phenol.

Yield of the desired phenolic compound increases with oxidation reaction zone pressure. It is recommended that the reaction be carried out under at least atmospheric pressure, preferably at a pressure of at least 2 atmospheres (absolute). Pressures substantially in excess of 2 atmospheres are more desirable, and there is no upper limit to the range of operable reaction pressure short of that at which, at the reaction temperature being employed, liquefaction of the phenolic compound and the aromatic aldehyde begins to take place. Operation of the reaction system above this liquefaction pressure will result in condensation reactions between the phenolic compound and the aldehyde with a consequent loss of chemical efficiency and the deposition of tars in the reaction system. A more quantitative description of the effect of pressure can be stated by the following mathematical expression: Rate = $K \times P_{oxygen} \times P_{toluene}^{1/2} \times P_{benzaldehyde}^{3/2}$, where K is the specific rate constant and the P's are the partial pressures of oxygen, toluene, and benzaldehyde.

It is recommended that the molar ratio of oxygen to aromatic aldehyde in the gaseous mixture introduced into the oxidation reaction zone at the start of the reaction step be between about 0.5:1 and 10:1 when practicing the embodiment of the invention in which a hydrocarbon, such as toluene, is not also being cooxidized with the aldehyde. When the aldehyde is being cooxidized with a hydrocarbon, as in that embodiment of the invention in which toluene is converted to phenol, it is recommemded that the molar ratio of oxygen to aromatic aldehyde be between about 1:1 and 20:1, it being understood that in this case a portion of the oxygen is actually being employed to oxidize part of the hydrocarbon, which is present in stoichiometric excess in the mixture being passed through the reaction zone. The molar ratio of total organic compounds to oxygen introduced into the reactor is preferably 1:1 to 10:1, more preferably 1:1 to 5:1.

It is advantageous that the retention time of the reactants in the reaction zone be between approximately 0.2 second and approximately 20 seconds, calculated at the temperature and pressure prevailing in the reaction zone and on the basis of the number of moles introduced into the zone (i.e., ignoring changes in molar throughput resulting from chemical reactions in the reaction zone). Longer retention times can be employed if desired, the only effect of unnecessarily extended retention time being some loss of chemical efficiency.

Reaction Equilibria

In that embodiment of the invention in which a hydrocarbon is not oxidized in admixture with the aromatic aldehydes the oxidation reaction, although involving free radical mechanisms and therefore comparatively complicated insofar as its mechanisms are concerned, is nevertheless straightforward as regards the mode of carrying it out. That is, so long as the temperature is controlled within the range discussed hereinabove and so long as the oxygen:aldehyde ratio is approximately as set forth above, the aldehyde will be converted to the desired phenolic product.

In that special embodiment in which aldehyde is oxidized together with a hydrocarbon precursor, however, it is to be noted that steady-state conditions do establish themselves in the reaction zone as a result of separating the phenolic compound from the reaction product and recycling to the reaction zone any or all of the precursors of the phenolic compounds which are contained in the reaction product. For example, in the cooxidation of toluene and benzaldehyde, the reaction product will contain benzaldehyde, phenol, benzyl alcohol, bibenzyl, and unconverted toluene as well as lesser quantities of various minor reaction by-products including biphenyl. Of these compounds it has been discovered that the biphenyl, while not per se deleterious in the reaction, is nevertheless substantially inert on being recycled to the reaction zone and therefore will continue to build up in the reaction product if all of the biphenyl formed in each pass through the reaction zone is recycled thereto. Therefore, in order to prevent an indefinitely continuing increase in the biphenyl content of the reaction system, it is recommended that biphenyl be removed from the reaction product as it is formed in the reactor. This can be done either continuously or intermittently. It will be recognized that a significant quantity of biphenyl may be present in the materials fed into the reaction zone (in which case it simply acts as a diluent); all that is required is that a biphenyl drawoff from the product recovery system be maintained as needed to avoid unlimited buildup of biphenyl in the system. This drawoff may be accomplished by simple distillation from the recovered reaction products, either continuously or, since the rate of biphenyl formation is very small, intermittently.

Nature of the Diluent

Te function of the diluent employed in practicing the invention is to prevent chemical reaction between the phenolic compound and unreacted aromatic aldehyde in the product recovery operations following the withdrawal of the hot gaseous reaction product from the reaction zone. The effect of the diluent is marked. For example, in small (laboratory size) apparatus having an oxidation reactor discharge connection only a few millimeters in diameter, it has been found possible to oxidize benzaldehyde with air (in the absence of diluent) for periods of only a few minutes before tar formation in the relatively cool reactor discharge line plugs the product recovery system and forces a reactor shutdown. In contradistinction, reaction can be continued indefinitely when the vapors of a suitable diluent (e.g. benzene or toluene) are injected upstream of the point at which liquid condensation on the walls of the apparatus could take place.

It is believed, although it is not intended that the scope of the invention be limited by this explanation, that the effect of the diluent in preventing reaction between the phenol and the aldeyde is due to the fact that these compounds react with one another much more slowly in an inert liquid diluent than they do when the diluent is absent. For example, highly concentrated liquid benzaldehyde and phenol will, when mixed together, react even at ambient or near-ambient temperatures. In the presence of a diluent, however, particularly when the diluent is present in an amount of about 90 mole percent or greater in the mixture, the reaction rate is generally retarded even at temperatures as high as about 150°C.

Although any diluent can be employed which is inert toward phenolic compounds and aromatic aldehydes at temperatures below about 500°C, non-polar diluents are preferred. Hydrocarbons are suitable, e.g., aromatic and alkyl-substituted aromatic hydrocarbons such as benzene, toluene, and xylenes. Benzene and toluene are especially useful. Toluene, of course, is useful both as a diluent and as a raw material which, by way of benzaldehyde, can be converted to phenol.

As has been noted above, the diluent can be injected wholly or in part into the reactants as they are introduced into the reaction zone; this would be a preferred mode of operation in that embodiment of the invention in which the diluent (toluene) is being cooxidizing with benzaldehyde and therefore serves as both diluent and a process raw material. Alternatively, the diluent can be injected, wholly or in part, as a vapor into the gaseous reaction products as, or just before, they leave the reaction zone. In this case it is recommended that in any event the diluent be introduced before the reaction product has been cooled to its dew point in order that any condensation thereof take place in the presence of liquid diluent. Yet another alternative is to quench the hot gaseous reaction product rapidly and completely with the liquid diluent. This can be accomplished by, for example, employing a jet condenser of one of the types widely known in the art, or by contacting the gases with the liquid in a spray tower, or by introducing the gases into the lower portion of an absorption tower against a downwardly-flowing stream of the diluent.

It is recommended that the diluent be a material in which the aldehyde and the phenolic compound are soluble, and that it be employed in an amount at least sufficient to dissolve all of the aldehyde and phenolic compound contained in the reaction product. It will be recognized that in those instances in which the diluent is initially injected into the system as a vapor these remarks contemplate that at least enough of the diluent will be condensed, along with the phenol and aldehyde, to form a liquid phase containing enough of the diluent in its liquid form to satisfy the criteria just set forth.

The Cooling Step

The gaseous reaction product, which leaves the reaction zone at a temperature in the range of roughly 300°C to 500°C, must be cooled and, at least insofar as the adelhyde and phenolic components are concerned, liquefied prior to recovering the phenolic product. Cooling should be rapid, since unnecessarily long retention at these temperatures tends to cause product degradation. The initial stages of cooling, down to that temperature which is the dew point of the product-containing gas being cooled, can be carried out either with or without an admixture of diluent. However, at or before the time when the gas has been cooled down to its dew point, the diluent should have been introduced so that when condensation or liquefaction begins the diluent will be present and constitute a component of the liquid being formed. For example, if the gas is cooled below its dew point in a surface heat exchanger, the diluent should be a component of the gaseous mixture introduced into the heat exchanger, either as vapor or as a liquid which has been injected into the gases entering the condenser. In that embodiment of the invention in which toluene is converted to phenol, unreacted toluene contained in the reactor product gases is condensed with the products and so serves as the diluent.

With further reference to the phenomena which have been found to take place when the reaction product begins to condense during the cooling step it has been found that, although the presence of the liquid diluent reduces tar formation and is needed for satisfactory operation of the process, the condensing temperature is also an important factor. Specifically it has been discovered that greatly improved conditions (as regards tar formation) obtain when the temperature at which the products begin to condense from the gaseous reaction mixture is not allowed to exceed about 200°C; even better results are obtained when this temperature is kept at or below about 160°C. While the use of a rapid quench as described above can effect this result, as can also the use of chilled surface condensers operated with high vapor velocities on the process side of the tubes, it is even more reliably effective to adjust, if necessary, the composition of the vapors entering the cooling step so that their dew point does not, at the pressure being employed in the cooling step, exceed about 200°C. In some instances such adjustment is not necessary, the gaseous reaction mixture composition and the cooling pressure being such that the dew point is already below 200°C. While the dew point exceeds 200°C, however, it is recommended that, before the mixture is cooled to the dew point, an adjustment of its composition or of the pressure in the cooling system be made to reduce the dew point to 200°C or less, preferably about 160°C or less. This adjustment can be made by either lowering the process pressure in the cooler or by introducing steam, additional quantities of the vapors of a diluent liquid, or a fixed gas such as nitrogen or methane into the gaseous reaction product entering the cooler. The decision as to which of these alternatives to employ can be readily made by anyone skilled in the art on the basis of process economic considerations affecting the particular installation. The engineering principles involved, i.e., the manner in which the dew point of a gas can be adjusted, are elementary and obvious to all chemical engineers. Specifically and for example, the dew point can be reduced by increasing the fixed gas content of a mixture, by introducing vapors of a volatile liquid, or by reducing the system pressure. The engineering calculations involved are all simple vapor pressure calculations employing the vapor pressures of the several components of the reaction mixture being processed.

In a run which benzaldehyde was being converted to phenol, the dew point adjustment just discussed has been carried out by simply injecting nitrogen into the oxidation reactor at its discharge end at a rate such that, at the cooling pressure being employed, 5 weight percent of the benzaldehyde contained in the reactor product would condense at a temperature of about 110°C, while the calculated dew point (calculated as the temperature at which 0.001% of the heaviest component - bibenzyl - would condense) was 160°C. Under these conditions there was no detectable tar formation. Steam, or the vapors of organic liquids having a boiling point not in excess of about 200°C at the pressure being employed in the cooler, can be employed in like manner in place of, or in addition to, the nitrogen.

It is recommended that the mixture of reaction products and diluents be cooled to a temperature below about 30°C if the cooled material is to be stored for any length of time (e.g., for as much as 6 or 8 hours) before the phenolic component is separated therefrom. This temperature is not critical, but at higher temperatures and at longer periods of retention there is danger of some product loss due to chemical reactions in the solution even in the presence of the diluent. Lower temperatures are actually preferred, i.e. temperatures below about 25°C and preferably the lowest temperatures which can be maintained without resorting to refrigeration.

Product Recovery

The invention is not restricted to any particular method for separating the phenolic compound from the other components of the mixture resulting from cooling of the reaction products in the presence of the diluent. Essentially, distillation can be employed to separate the mixture into whatever fractions may be desired, by methods which will be obvious to one skilled in the art.

The separation of the phenolic compound from the aromatic aldehyde, however, presents problems not readily solved by the prior art. If, for example, the diluent is distilled away from a residue comprising the phenolic compound and the aldehyde without first removing one or the other of these reactive compounds, they will react with resulting loss of product and fouling of the process equipment. It has now been discovered that this separation can be effected by extraction with certain solvents. More particularly it has been discovered that, taking a reaction product comprising toluene, phenol, and benzaldehyde as an example, the phenol can be separated from the benzaldehyde by extraction with a solvent consisting essentially of methanol and water, preferably in 1:1 ratio of methanol to water by weight. The first step in this extraction is to extract the reaction product just described with the methanol-water mixture (preferably countercurrently, in apparatus providing at least 10 theoretical stages, and with a 1:1 ratio of methanol-water to reaction product). The phenol, a trace of the benzaldehyde, and a portion of the benzyl alcohol initially contained in the reaction product will be recovered in the extract.

The extract is then back-extracted with toluene (in an amount of approximately 1 part or more of toluene to 10 parts of said extract in apparatus affording at least about 2 theoretical stages), whereby the benzaldehyde is recovered in the toluene for recycle to the reaction step of the process. The raffinate from the toluene extraction just described comprises phenol and benzyl alcohol, which can be separated by distillation to recover the phenol.

From the first extraction step with methanol-water, described above, the raffinate comprises process diluent (e.g. toluene) in which is dissolved most of the benzyl alcohol formed in the reaction step, substantially all of the bibenzyl, and a part of the benzaldehyde. Any biphenyl formed in the reaction step will also be contained in the raffinate. Also present will be some methanol (approximately 6% more or less of the raffinate). This raffinate is conveniently recycled to the oxidation step of the process. Preferably the methanol is removed by water extraction before the raffinate is recycled. The biphenyl can be removed, to whatever degree of removal is desired, by simple distillation. As previously noted, it is not necessary to remove all of the biphenyl.

Mixtures of ethylene glycol and water, especially a mixture consisting essentially of 75% ethylene glycol and 25% water by weight, are as effective as or more effective than the methanol-water mixture just described in extracting the phenol from the cooled reaction product, in that distribution coefficients of phenol and benzaldehyde between this solvent and the process diluent liquid are even more favorable than with the methanol-water solvent. In place of ethylene glycol, other polyhydric alcohols can be employed in admixture with water e.g., propanediols, butanediols, and lower alkanetriols.

The following examples are given to illustrate the invention further. It will be recognized that many variations can be made therein without departing from the spirit of the invention.

EXAMPLE I

An oxidation reactor was employed which comprised a vertical glass tube having an inside diameter of 39 millimeters and a length, excluding inlet and outlet connections, of 20 centimeters. The reactor was equipped with means for measuring the internal temperature, and it was wrapped with electrical heating elements whereby heat losses could be avoided. (The reaction is exothermic, but in equipment of this size external heating is needed to maintain reactor temperature and also to prevent condensation of liquid on the walls of the reactor).

Communicating with the lower end of the reactor was a feedstock vaporization section consisting of a downward extension of the reaction tube approximately 10 centimeters long, which was packed with Berl saddles and wrapped with an electric heating element. Connected to the bottom of the vaporizer there was an inlet for introducing nitrogen which was employed to sweep vapors out of the vaporizer and into the reactor.

The reactor was surmounted with a vertical spiral condenser, which discharged into a product receiver. The product receiver was a 500 milliliter glass vessel provided with a drawoff valve at the bottom and with a vent line at the top, through which vent line uncondensed gases passed through a chilled secondary condenser connected to a secondary liquid product receiver which was vented through a dry test meter.

In operation of the reactor, liquid reactants were introduced at a controlled rate into the vaporizer section, where they were vaporized and, with the assistance of the nitrogen sweep, moved in vapor form into the bottom of the reactor and then through the reactor and into the condenser. Molecular oxygen, normally in the form of air, was also introduced at a controlled rate into the bottom of the reactor.

Into the reactor, operating as described above at a temperature of approximately 300°C and at a pressure of 3.7 atmospheres absolute, there was continuously introduced 1.8 gram moles per hour of benzene and 0.15 gram moles per hour of benzaldehyde, together with 2.1 gram moles per hour of air and 2.1 gram moles per hour of sweep nitrogen.

The reactor was operated in this manner for 15 minutes, the condensed reaction products being accumulated in the distillate receiver described above and the uncondensed vent gases being measured by means of the dry test meter. During the run the temperature in the reactor varied between about 290°C and 305°C.

Measurement and chemical analysis of the condensed reaction products indicated the following: Total liquid products obtained amounted to 32 grams and contained 89.5 weight percent benzene, 2.1 weight percent phenol, 7.8 weight percent benzaldehyde, and 0.6 weight percent biphenyl. There was no detectable content of benzoic acid. Of the benzaldehyde initially fed into the reactor, 24 percent had been converted to phenol, 8.3 percent to biphenyl, and 6 percent to carbon oxides, while 62 percent had passed through the reactor unconverted. Approximately 99 percent of the benzene initially fed into the reactor was recovered in the liquid products or accounted for as vapor in the gases discharged through the dry test meter.

When operating in the same manner as described above but without the admixture of benzene diluent, rapid formation of tars and carbonaceous solids in the condenser and upper portion of the reactor plugged the reaction system after only a few minutes of operation.

EXAMPLE II

The same reaction system described in Example I was employed to cooxidize benzaldehyde and toluene in the presence of an excess of toluene (i.e., sufficient toluene was admixed into the reaction feedstock that a substantial quantity of unoxidized toluene remained in the gaseous product).

Reactor temperature was approximately 300°C, ranging from 290°C at the inlet to 313°C at the outlet. Reactor pressure was 4.5 atmospheres absolute. Reactor retention time was 11.5 seconds, calculated at reactor temperature and pressure and based on the number of moles of reactants introduced into the reactor. The feed consisted of toluene (17.1 mole percent), benzaldehyde (0.9 mole percent), molecular oxygen (15 mole percent), and nitrogen (67 mole percent including nitrogen introduced into the vaporizer as sweep gas). The molar ratio of benzaldehyde and toluene to molecular oxygen was 1.2.

Of the total benzaldehyde and toluene introduced into the reactor, 2 percent was oxidized. Approximately one mole of toluene was consumed per mole of benzaldehyde consumed. Analysis of the reaction products indicated that, per 100 moles of benzaldehyde introduced into the reactor, there was recovered in the reaction products 19 moles of phenol, 100 moles of benzaldehyde, 3.5 moles of bibenzyl, 3.3 moles of benzoic acid, and 9 moles of benzyl alcohol. The moles of product in excess of the 100 moles of benzaldehyde recovered are equivalent to the moles of toluene oxidized.

EXAMPLE III

The same reaction system described in Example I was employed to cooxidize benzaldehyde, benzyl alcohol, and toluene in the presence of an excess of toluene.

Reactor temperature was approximately 360°C, ranging from 335°C at the inlet to 365°C at the outlet. Reactor pressure was 5 atmospheres absolute. Reactor retention time was 9.2 seconds, calculated at reactor temperature and pressure and based on the number of moles of reactants introduced into the reactor. The feed consisted of toluene (29 mole percent), benzaldehyde (1.1 mole percent), benzyl alcohol (1.3 mole percent), molecular oxygen (12.5 mole percent), and nitrogen (56.1 mole percent including nitrogen introduced into the vaporizer as sweep gas). The molar ratio of benzaldehyde, benzyl alcohol, and toluene to molecular oxygen was 2.5. The organic feed composition was such that 84 moles of benzaldehyde were present per 100 moles of benzyl alcohol.

Of the total benzaldehyde, benzyl alcohol, and toluene introduced into the reactor, 2.9 percent was oxidized. Approximately one mole of toluene was consumed per mole of benzyl alcohol consumed. Analysis of the reaction products indicated that, per 100 moles of benzyl alcohol introduced into the reactor, there were recovered in the reaction products 28 moles of phenol, 99 moles of benzaldehyde, 6.5 moles of bibenzyl, 84 moles of benzyl alcohol, and 89 moles of carbon monoxide and carbon dioxide.

The foregoing yield data indicate that benzyl alcohol was oxidized at a higher rate than its production rate from toluene. The efficiency to phenol based upon toluene, benzaldehyde, and benzyl alcohol was 36%. The increase in benzaldehyde concentration due to oxidation of toluene and benzyl alcohol represents a net efficiency to benzaldehyde of 26%.

EXAMPLE IV

The same reaction system described in Example 1 was employed to cooxidize benzaldehyde, benzyl alcohol, bibenzyl, and toluene in the presence of an excess of toluene.

Reactor temperature was approximately 350°C, ranging from 348°C at the inlet to 352°C at the outlet. Reactor pressure was 5 atmospheres absolute. Reactor retention time was 9.3 seconds, calculated at reactor temperature and pressure and based on the number of moles of reactants introduced into the reactor. The feed consisted of toluene (27.8 mole percent), benzaldehyde (2.3 mole percent), benzyl alcohol (1.4 mole percent), bibenzyl (0.8 mole percent), molecular oxygen (12.2 mole percent), and nitrogen (55.5 mole percent including nitrogen introduced into the vaporizer as sweep gas). The molar ratio of benzaldehyde, benzyl alcohol, bibenzyl, and toluene to molecular oxygen was 2.6.

Of the total benzaldehyde, benzyl alcohol, bibenzyl, and toluene introduced into the reactor, 3.5 percent was oxidized. Approximately one mole of toluene was consumed per mole of combined benzaldehyde, benzyl alcohol, and bibenzyl consumed. Analysis of the reaction products indicated (a) that per mole of benzaldehyde introduced into the reactor 0.93 mole was recovered in the reaction product, (b) that per mole of benzyl alcohol introduced 0.80 mole was recovered in the product, and (c) that per mole bibenzyl introduced, 0.94 mole was recovered in the product. The weight accountability of organic feed across the reactor was 99 percent. The product contained 0.33 mole of phenol per mole of benzaldehyde introduced into the reactor. The total oxidate was equivalent to 0.50 mole per mole benzaldehyde introduced into the reactor, which is approximately equivalent to the number of moles of toluene consumed. The amount of phenol in the product corresponds to a phenol efficiency of 66 percent. Small quantities of biphenyl were also present, in a amount equivalent to 5 mole percent or less of the toluene and benzaldehyde consumed. The remainder of the oxidate was carbon oxides.

EXAMPLE V

The same reaction system as described in the previous examples was employed.

Reactor temperature was approximately 350°C, ranging from 363°C at the inlet to 332°C at the outlet. Reactor pressure was 5 atmospheres absolute. Reactor retnetion time was 6 seconds, calculated at reactor temperature and pressure and based on the number of moles of reactants introduced into the reactor. The feed consisted of toluene (17.7 mole percent), benzaldehyde (1.5 mole percent), benzyl alcohol (0.9 mole percent), bibenzyl (0.5 mole percent), molecular oxygen (15.3 mole percent), and nitrogen (64.1 mole percent including nitrogen introduced into the vaporizer as sweep gas). The molar ratio of benzaldehyde, benzyl alcohol, bibenzyl, and toluene to molecular oxygen was 1.3.

Of the total benzaldehyde, benzyl alcohol, bibenzyl, and toluene introduced into the reactor, 3.2 percent was oxidized. Approximately one mole of toluene was consumed per mole of combined benzaldehyde, benzyl alcohol, and bibenzyl consumed. Analysis of the reaction products indicated (a) that per mole of benzaldehyde introduced into the reactor, 0.98 mole was recovered in the reaction product, (b) that per mole benzyl alcohol introduced into the the reactor 0.80 mole was recovered in the product, and (c) that per mole bibenzyl introduced into the reactor 0.96 mole was recovered in the reaction product. The weight accountability across the reactor was 99 percent. The product contained 0.30 mole of phenol per mole of benzaldehyde introduced into the reactor. The total oxidate was equivalent to 0.46 mole per mole of benzaldehyde introduced into the reactor, which is approximately equivalent to the moles of toluene consumed. The amount of phenol in the product corresponded to a phenol efficiency of 65 percent. Small quantities of biphenyl were also present, in an amount equivalent to 5 mole percent or less of the toluene and benzaldehyde consumed. The remainder of the oxidate was carbon oxides.

EXAMPLE VI

The same reaction system described in the previous examples was employed.

Reactor temperature was approximately 295°C, ranging from 307°C at the inlet to 283°C at the outlet. Reactor pressure was 5 atmospheres absolute. Reactor retention time was 10 seconds, calculated at reactor temperature and pressure and based on the number of moles of reactants introduced into the reactor. The feed consisted of toluene (28.3 mole percent), benzaldehyde (2.3 mole percent), benzyl alcohol (1.4 mole percent), bibenzyl (0.8 mole percent), molecular oxygen (12.1 mole percent), and nitrogen (55.1 mole percent including nitrogen introduced into the vaporizer as sweep gas). The molar ratio of benzaldehyde, benzyl alcohol, bibenzyl, and toluene to molecular oxygen was 2.7.

Of the total benzaldehyde, benzyl alcohol, bibenzyl, and toluene introduced into the reactor, 2 percent was oxidized. Approximately one mole of toluene was consumed per mole of benzaldehyde consumed. Analysis of the reaction products indicated (a) that, per mole of benzaldehyde introduced into the reactor, 0.94 mole was recovered in the reaction product, (b) that per mole benzyl alcohol introduced into the reactor, 0.88 mole was recovered in the reaction product, and (c) that per mole of bibenzyl introduced into the reactor, 0.80 mole was recovered in the reactor product. The product contained 0.15 mole of phenol per mole of benzaldehyde introduced into the reactor and 0.10 mole of benzoic acid per mole benzaldehyde introduced into the reactor. The total oxidate was equivalent to 0.29 mole per mole of benzaldehyde introduced into the reactor. The phenol and benzoic acid in the oxidate corresponded to 52 and 33 percent efficiency respectively. Small quantities of biphenyl were also present, in an amount equivalent to 5 mole percent or less of the toluene and benzaldehyde consumed. The remainder of the oxidate was carbon oxides.

The following illustrates the separation of phenol from benzaldehyde by extraction with a water-ethylene glycol mixture, the phenol and benzaldehyde being in solution in toluene:

EXAMPLE VII

One part by weight of a liquid consisting of 81.0 weight percent toluene, 5.0 weight percent phenol, 9.0 weight percent benzaldehyde, and 5.0 weight percent benzyl alcohol was mixed thoroughly with one part by weight of a liquid consisting of 75 weight percent ethylene glycol and 25 weight percent water at atmospheric pressure and at a temperature of approximately 25°C. The resulting mixture was allowed to stand for approximately 30 minutes, at the end of which time it had separated into two liquid phases. The lower (aqueous) phase amounted to approximately 54 weight percent of the total liquid present and, upon analysis, was found to comprise 70.0 weight percent ethylene glycol, 23.4 weight percent water, 3.2 weight percent phenol, 2.8 weight percent benzyl alcohol, and 0.6 weight percent benzaldehyde. The upper (non-aqueous) phase amounted to 46 weight percent of the total liquid present and contained 87.1 weight percent toluene, 1.7 weight percent phenol, 2.2 weight percent benzyl alcohol, and 9.0 weight percent benzaldehyde. Of the phenol originally contained in the toluene prior to admixture with the ethylene glycol-water mixture, 68 percent was recovered in the glycol-water phase and 32 percent remained in the toluene phase. Of the benzyl alcohol originally contained in the toluene solution, 60 percent was recovered in the glycol-water phase and 40 percent remained in the toluene phase. Of the benzaldehyde initially contained in the toluene solution, 93 percent was recovered in the toluene phase and 7 percent in the glycol-water phase. Upon drawing off the glycol-water phase and re-extracting it with toluene, substantially all of the benzaldehyde contained therein is recovered in the tolene extract while substantially all of the phenol contained therein remains in the glycol-water phase.

The following illustrates a method, based on extraction with a lower dialkyl ether, for recovering the glycol from a mixture of phenol, aromatic alcohol, water, and glycol such as that obtained in Example VII above:

EXAMPLE VIII

One part by weight of a liquid containing 70 weight percent ethylene glycol, 15 weight percent water, 8 weight percent phenol, and 7 weight percent benzly alcohol was mixed thoroughly with one part by weight of diethyl ether at atmospheric pressure and a temperature of approximately 25°C. The resulting mixture was allowed to stand for approximately 30 minutes, at the end of which time it had separated into two liquid phases. The upper (non-aqueous) phase amounted to approximately 54 weight percent of the total liquid present and upon analysis was found to contain 87.7 weight percent diethyl ether, 5.3 weight percent phenol, 6.3 weight percent benzyl alcohol, and 0.7 weight percent ethylene glycol. The lower (aqueous) phase amounted to 46 weight percent of the total liquid present, and contained 73 weight percent glycol, 24 weight percent water, 0.5 weight percent benzyl alcohol, and 2.6 weight percent phenol. Of the phenol originally contained in the glycol-water solution prior to admixture with the ether, 70 percent was recovered in the ether phase and 30 percent remained in the glycol-water phase. Of the benzyl alcohol initially in the glycol-water solution, 95 percent was recovered in the ether phase and 5 percent remained in the glycol-water phase. Upon separating the upper ether phase and re-extracting with a portion of water, substantially all the ethylene glycol contained therein is recovered, while substantially all the phenol and benzyl alcohol contained therein remain in the ether phase. The diethyl ether, phenol, and benzyl alcohol are easily separated by distillation.

Substantially the same results as described above were obtained when di-n-butyl ether was substituted on a weight-for-weight basis for the diethyl ether employed above. The di-n-butyl ether has advantages over the diethyl ether in its volatility characteristics and relatively lower susceptibility to the formation of explosive peroxides. Di-lower alkyl ethers broadly are applicable in this extraction, although diethyl and di-n-butyl ether are the species most readily available and therefore particularly suitable.

The embodiments of the invention in which an exclusive property or privilege is claimed are defined as follows:

1. A process for converting an aromatic aldehyde of the formula:

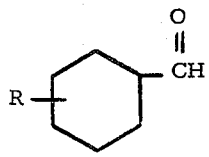

to a phenolic compound of the formula:

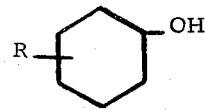

wherein R is a member of the group consisting of hydrogen and methyl groups, which process comprises the steps of:

a. reacting said aldehyde with molecular oxygen by continuously passing a gaseous mixture comprising said aldehyde and oxygen through a reaction zone maintained under at least atmospheric pressure at a temperature between about 250°C and about 450°C to form a gaseous reaction product comprising said phenolic compound; and b. cooling said reaction product in intimate contact with an inert liquid diluent.

2. The process of claim 1 wherein the reaction is conducted noncatalytically and at a reaction zone pressure of at least about two atmospheres absolute.

3. The process of claim 2 wherein the molar ratio of oxygen to aromatic aldehyde in said gaseous mixture at the start of the reaction step is between about 0.5:1 and 20:1.

4. The process of claim 3 wherein the retention time of the gaseous mixture in the reaction zone is between about 0.2 seconds and about 20 seconds, calculated at reaction zone pressure and temperature.

5. The process of claim 4 wherein the reaction is conducted at a temperature between about 275°C and about 425°C.

6. The process of claim 5 wherein the diluent comprises a member of the group consisting of benzene, toluene, o-xylene, m-xylene, and p-xylene.

7. The process of claim 6 wherein R is hydrogen, the diluent comprises a member of the group consisting of benzene and toluene, and the diluent is brought into contact with the reaction product in a proportion such that, after cooling, the resulting cooled liquid mixture of diluent and reaction product contains at least about 70 mole percent diluent.

8. The process of claim 7 wherein the cooling step comprises preparing a mixture having a dew point not greater than about 200°C at the pressure obtaining during said cooling step and comprising (a) the diluent in its vapor state and (b) the gaseous reaction product, followed by cooling the resulting mixture.

9. The process of claim 8 further characterized in that the mixture of diluent and reaction product is prepared by incorporating at least a portion of the diluent into the gaseous mixture passing through the reaction zone and wherein the dew point of the gaseous reaction product is adjusted to a temperature not exceeding about 160°C at the pressure existing during said cooling step.

* * * * *

UNITED STATES PATENT AND TRADEMARK OFFICE
CERTIFICATE OF CORRECTION

PATENT NO. : 3,962,350
DATED : 6/8/76
INVENTOR(S) : Theodore Horlenko, James Henry George It is certified that error appears in the above-identified patent and that said Letters Patent are hereby corrected as shown below:

In column 2, line 12, for "alkybenzene" read -- alkylbenzene.

In column 2, line 44, for "prevent" read -- prevented.

In column 5, line 9, after "which" insert -- it --.

In column 5, line 54, for $P_{toluene}1/2 \times P_{benzaldehyde}3/2$ read -- $P_{toluene}^{1/2} \times P_{benzaldehyde}^{3/2}$.

In column 6, line 66, for "Te" read -- The.

In column 7, line 43, for "cooxidizing" read -- cooxidized.

Signed and Sealed this

Tenth Day of May 1977

[SEAL]

Attest:

RUTH C. MASON
*Attesting Officer*

C. MARSHALL DANN
*Commissioner of Patents and Trademarks*